United States Patent [19]

Shibusawa et al.

[11] Patent Number: 5,114,589
[45] Date of Patent: May 19, 1992

[54] TYPE-XLL CROSS-AXIS SYNCHRONOUS FLOW-THROUGH COIL PLANET CENTRIFUGE FOR SEPARATION OF BIOPOLYMERS

[75] Inventors: Yoichi Shibusawa, Rockville; Yoichiro Ito, Bethesda, both of Md.

[73] Assignee: The United States Government as represented by the Secretary of the Department of Health and Human Services, Washington, D.C.

[21] Appl. No.: 642,340

[22] Filed: Jan. 17, 1991

[51] Int. Cl.$^5$ .............................................. B10D 15/08
[52] U.S. Cl. .................................. 210/657; 210/634; 210/635; 210/198.2
[58] Field of Search ..................... 210/198.2, 657, 635, 210/634, 656

[56] References Cited

U.S. PATENT DOCUMENTS

| | | | |
|---|---|---|---|
| 4,162,761 | 7/1979 | Ito | 210/198.2 |
| 4,414,108 | 11/1983 | Ito | 210/198.2 |
| 4,430,216 | 2/1984 | Ito | 210/198.2 |
| 4,487,693 | 12/1984 | Ito | 210/657 |
| 4,714,554 | 11/1987 | Ito | 210/657 |
| 4,753,734 | 6/1988 | Ito | 210/657 |
| 4,857,187 | 8/1989 | Ito | 210/657 |
| 4,980,065 | 12/1990 | Hsu | 210/634 |

OTHER PUBLICATIONS

Ito et al., J. of Chromatography, 463(1989) 305-316.
Bhatnagar et al., J. of Chromatography, 436(1989) 317-328.
Ito et al., J. of Chromatography, 449 (1988) 135-151.

Primary Examiner—Robert A. Dawson
Assistant Examiner—Sun Uk Kim
Attorney, Agent, or Firm—Lowe, Price, LeBlanc & Becker

[57] ABSTRACT

A type-XLL cross-axis synchronous flow-through coil planet centrifuge including exclusively left-handed column coils and a method of separating macromolecules utilizing the same. The exclusive use of left-handed column coils allows retention of the stationary phase when utilizing aqueous-aqueous two-phase solvent systems. The cross-axis synchronous flow-through coil planet centrifuge has been utilized to separate proteins utilizing an aqueous-aqueous polymer phase solvent system.

14 Claims, 5 Drawing Sheets

TYPE X  TYPE XL  TYPE XLL  TYPE L

L=0  L=R  L=2R  R=0

COLUMN HOLDER

X: AXIS OF REVOLUTION;  — — — AXIS ROTATION;  R: ROTATION RADIUS;  L: REVOLUTION RADIUS

TYPE-XLL CROSS-AXIS SYNCHRONOUS FLOW-THROUGH COIL PLANET CENTRIFUGE FOR SEPARATION OF BIOPOLYMERS

TECHNICAL FIELD

The present invention relates to a cross-axis synchronous flow-through coil planet centrifuge. More particularly, the present invention relates to a cross-axis synchronous flow-through coil planet centrifuge which has been modified for use in the separation of macromolecules utilizing aqueous-aqueous two-phase solvent systems. The present invention also relates to methods of separating macromolecules which utilizes the cross-axis synchronous flow-through coil planet centrifuge.

BACKGROUND ART

Recently, the cross-axis synchronous flow-through coil planet centrifuge (X-axis CPC) (Ito, Sep. Sci. Tech., 22 (1987) 1971, and 1989) has been remarkably improved with regard to the stationary phase retention, revolution speed, etc. The cross-axis synchronous flow-through coil planet centrifuge has a unique feature among coil planet centrifuges in that the column holder axis is perpendicular to the central axis of the centrifuge (Ito, sep. Sci. Tech., 22 (1987) 1971). In the past, three different models of the X-axis CPC were fabricated and their capability for performing countercurrent chromatography (CCC) was examined using various two-phase solvent systems (Ito, Sep. Sci. Tech., 22 (1987) 1971, and 1989; Ito et al, J. Chromatoqr., 449 (1988) 135 and 153; Zhang et al, J. Chromatoqr., 454 (1988) 185; Ito et al, 455 (1988) 151; Ito et al, J. Chromatoqr., 463 (1989) 305; and Bhatnagar et al, J. Chromatoqr., 463 (1989) 317).

Hydrodynamic studies on retention of the stationary phase in the coiled column of the x-axis CPC indicate that the system provides more reliable retention of the stationary phase for viscous polar solvent systems compared with the high-speed CCC centrifuge based on the type J synchronous planetary motion (Ito, Sep. Sci. Tech., 22 (1987) 1971, and 1989).

Further studies have shown that the phase retaining capacity of the X-axis CPC is enhanced by laterally shifting the position of the column holder along the holder shaft, probably due to the asymmetry of the laterally acting force field between the upper and the lower halves of the rotating coil (Ito et al, J. Chromatoqr., 449 (1988) 135). The degree of the lateral shift of the column holder may be conveniently expressed by L/R where L is the distance from the center of the holder shaft to the coil holder and R the distance from the centrifuge axis to the holder shaft (revolution radius) (FIG. 1). The latest model (Bhatnagar et al, J. Chromatoqr., 463 (1989) 317) with L/R=1 (FIG. 1B) has produced substantially higher stationary phase retention for the polar solvent systems compared with the original model (Ito, Sep. Sci. Tech., 22 (1987) 1971, and 1989) with the central column position (L=0, FIG. 1A).

The present invention involves an improvement over known coil planet centrifuges which allows for separation of macromolecules utilizing aqueous-aqueous two-phase solvent systems.

DISCLOSURE OF THE INVENTION

It is accordingly one object of the present invention to provide a cross-axis synchronous flow-through coil planet centrifuge which is modified for use with aqueous-aqueous two-phase solvent systems.

Another object of the present invention is to provide a cross-axis synchronous flow-through coil planet centrifuge which includes a pair of coil holders each supporting left-handed multilayer coil columns.

A further object of the present invention is to provide a method of separating polar compounds in a cross-axis synchronous flow-through coil planet centrifuge.

A still further object of the present invention is to provide a method of separating macromolecules utilizing aqueous-aqueous two-phase solvent systems.

It is still a further object of the present invention to provide a method of separating macromolecules in a cross-axis synchronous flow-through coil planet centrifuge which utilizes aqueous-aqueous two-phase solvent systems.

According to these and further objects of the present invention which will become apparent as the description thereof is present below, there is provided a cross-axis synchronous flow-through coil planet centrifuge including a pair of column holders mounted on each side of a rotary frame and a pair of coiled columns mounted on said column holders, wherein each of the pair of coiled columns consists of left-handed coils.

The present invention further provides for a method of partitioning macromolecules utilizing a cross-axis synchronous flow-through coil planet centrifuge which involves:

providing an aqueous-aqueous two-phase solvent system including a stationary phase and a mobil phase;

filling the centrifuge with the stationary phase of the aqueous-aqueous two-phase solvent system;

injecting a sample containing macromolecules into the centrifuge;

supplying the mobil phase of the aqueous-aqueous two-phase solvent system to the centrifuge while rotating the centrifuge; and eluting the macromolecules from the sample.

BRIEF DESCRIPTION OF DRAWINGS

The present invention will be described hereafter with reference to the annexed drawings, which are given by way of non-limiting examples only in which.

BEST MODE FOR CARRYING OUT THE INVENTION

The present invention involves a cross-axis synchronous flow-through coil planet centrifuge which has been modified to improve retention of the stationary phase in aqueous-aqueous polymer phase systems. According to the present invention, it has been discovered that individual coil layers in a cross-axis flow-through coil planet centrifuge yield a much higher retention of the stationary phase when the individual coil layers are all exclusively left-handed.

This exclusive left-handed configuration of the individual layers of the coils can be achieved according to the present invention either by connecting each layer with a narrow transfer tube or using a continuous piece of tubing which is directly returned to the starting position after completing each coiled layer. Although this modification actually causes minor deformation of the multilayer coil by accommodating the connection flow tube between each layer, it has been discovered that the modification produces a unique hydrodynamic mechanism which provides good retention of the stationary phase of viscous polar solvent systems such as butanol which tend to produced carryover problems in other types of the CCC apparatus.

The cross-axis flow-through coil planet centrifuge which has been modified according to the present invention has been discovered to be useful to separate various macromolecules, including biopolymers such as proteins, nucleic acids and polysaccharides, and cells and cell organelles.

Figure 1A:
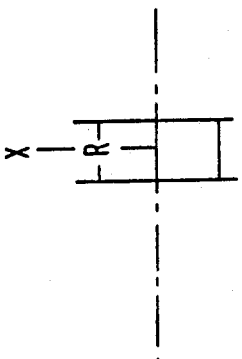
FIGS. 1A-1D are diagrams illustrating the column holder on the axis of rotation in four types of coil planet centrifuges.
Figure 1B:
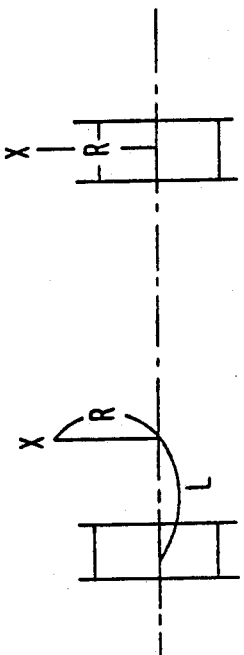
Figure 1C:
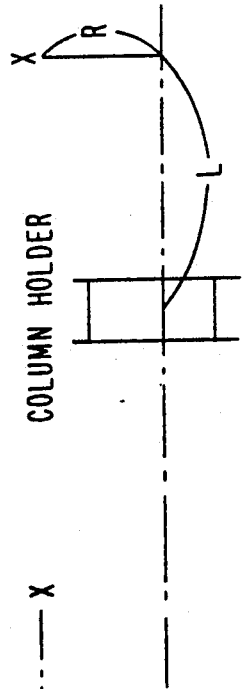
Figure 1D:
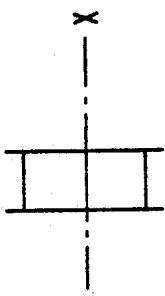
Figure 2:
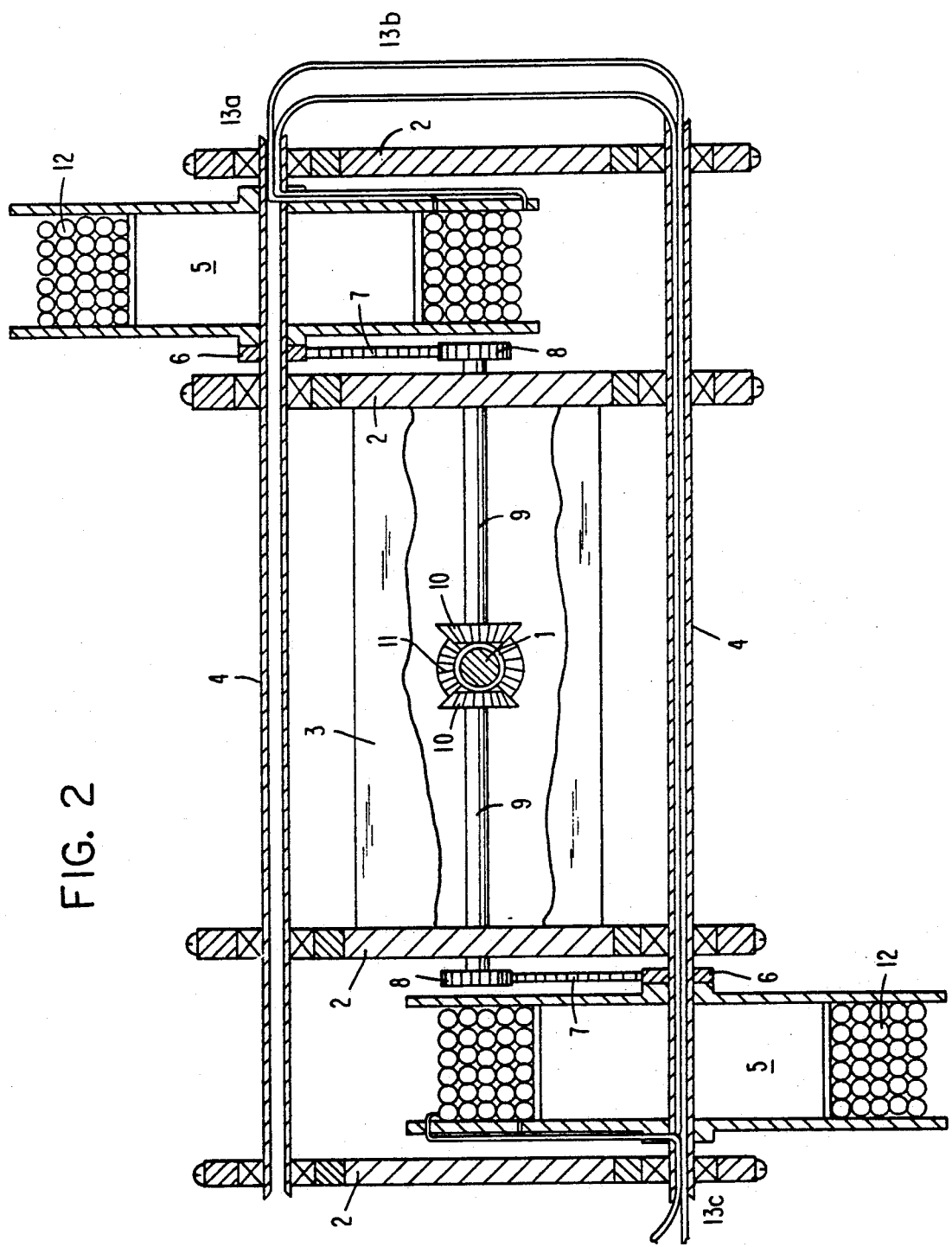
FIG. 2 is a cross sectional view of the type XLL coil planet centrifuge.

The basic design of the apparatus subsequently modified for use in accordance with the present invention has been reported earlier by Ito et al, *J. Chromatoqr.*, 463 (1989) 305, the disclosure of which is expressly incorporated herein by reference. The apparatus has a degree of lateral shift (L/R) of 2 to provide a strong lateral force field to retain viscous polar solvent systems. However, a degree of lateral shift greater than 2 was determined to be useful for purposes of the present invention. FIG. 2 schematically illustrates the horizontal cross section of the apparatus equipped with a pair of multilayer coils.

A motor (not illustrated) drives a central shaft 1 and a rotary frame around the central axis of the centrifuge. The rotary frame consists of 2 pairs of side plates 2 rigidly bridged by a pair of horizontal plates 3 and holds a pair of rotary shafts 4 horizontally at a distance of 7.6 cm from the central axis of the centrifuge. A pair of spool-shaped column holders 5 are mounted one on each side of the rotary frame between the outer and inner side plates 2 at a distance 15 cm from the center of the rotary shaft. The desired synchronous planetary motion of the holders is produced as follows: The toothed pulley 6 mounted on each holder shaft is coupled with a toothed belt 7 to an identical pulley 8 on the countershaft 9 equipped with a miter gear (45° angle) 10 which is in turn engaged to the identical stationary sun gear 11 mounted on the bottom plate of the centrifuge. A pair of coiled columns 12 mounted on the holders are serially connected with flow tubes (13a–c) as illustrated in FIG. 2. The above mechanical arrangement prevents twisting of the flow tubes and continuous elution can be performed through the rotating column without the use of rotary seals. Four pairs of interchangeable coil holders were fabricated with different hub diameters of 3.8 cm, 7.6 cm, 16 cm and 24 cm. The coil holders are easily removed from the rotary frame by loosening the screws on each bearing block.

The apparatus was operated up to the maximum speed of 1000 rpm with a speed controller (Bodine Electric Co., Chicago, IL, USA).

The performance of the basic apparatus, prior to modification was experimentally evaluated utilizing various combinations of the following reagents: n-Hexane, ethyl acetate, chloroform, methanol, n-butanol, sec.-butanol (all chromatographic grade), and acetic acid (reagent grade).

Utilizing these reagents, the following pairs of solvent systems were then prepared: n-hexane/water, n-hexane/methanol, n-hexane/ethyl acetate/methanol/water (1:1:1:1, v/v/v/v), ethyl acetate/water, ethyl acetate/acetic acid/water 4:1:4, v/v/v), chloroform/water, chloroform/acetic acid/water (2:2:1, v/v/v), n-butanol/water, n-butanol/acetic acid/water (4:1:5, v/v/v) and sec.-butanol/water. Each solvent mixture was thoroughly equilibrated in a separatory funnel at room temperature and the two phases separated shortly before use.

Initial evaluations of the apparatus were preformed utilizing short coils of approximately 3–5 m long, 2.6 mm I.D. PTFE (polytetrafluoroethylene) tubing wound directly around the holders of 7.6 cm and 24 cm hub diameters forming a single-layer coil with a total capacity of 20–30 ml. Both right-handed and left-handed coils were made for each holder. The handedness of the coils are conventionally determined and defined by the direction in which the coils are wound on the spool-shaped column holders. Each coiled column was firmly affixed on the holder with several pieces of fiber-glass reinforced adhesive tape. Each end of the column was directly connected to a 1 m × 0.85 mm I.D. PTFE flow tube. The connection was made by inserting a series of smaller diameter PTFE tubing into one another.

Experimental runs described in the examples given below were performed according to the standard procedure described by Bhatnagar et al, *Chromatoqr.*, 463 (1989) 317, the disclosure of which is expressly incorporated herein by reference. In each run, the coil was first filled entirely with the stationary phase. Then the apparatus was rotated at the desired revolution speed while the mobile phase was pumped into the column at a flow rate of 2 ml/min. using a 50 ml or 20 ml capacity glass syringe driven by a syringe driver.

The effluent from the outlet of the column was collected into a 25 ml or 50 ml graduated cylinder to measure the volume of the stationary phase eluted from the column as well as the total elution volume of the mobile phase. The elution was continued for 12–15 min. until the total elution volume exceeded the column capacity. During the elution, the temperature inside the centrifuge was controlled at 22° C. ±2° C. by placing an ice-bag over the top plate of the centrifuge. Then the centrifuge was stopped and the column contents emptied into a graduated cylinder by connecting the inlet of the column to a pressured $N_2$ line (ca 80 psi). The column was then washed with several milliliters of methanol and finally flushed with several milliliters of the stationary phase which was to be used for the next run.

The following examples are presented to illustrate the invention which is not intended to be considered as being limited thereto.

EXAMPLE 1

Figure 3:
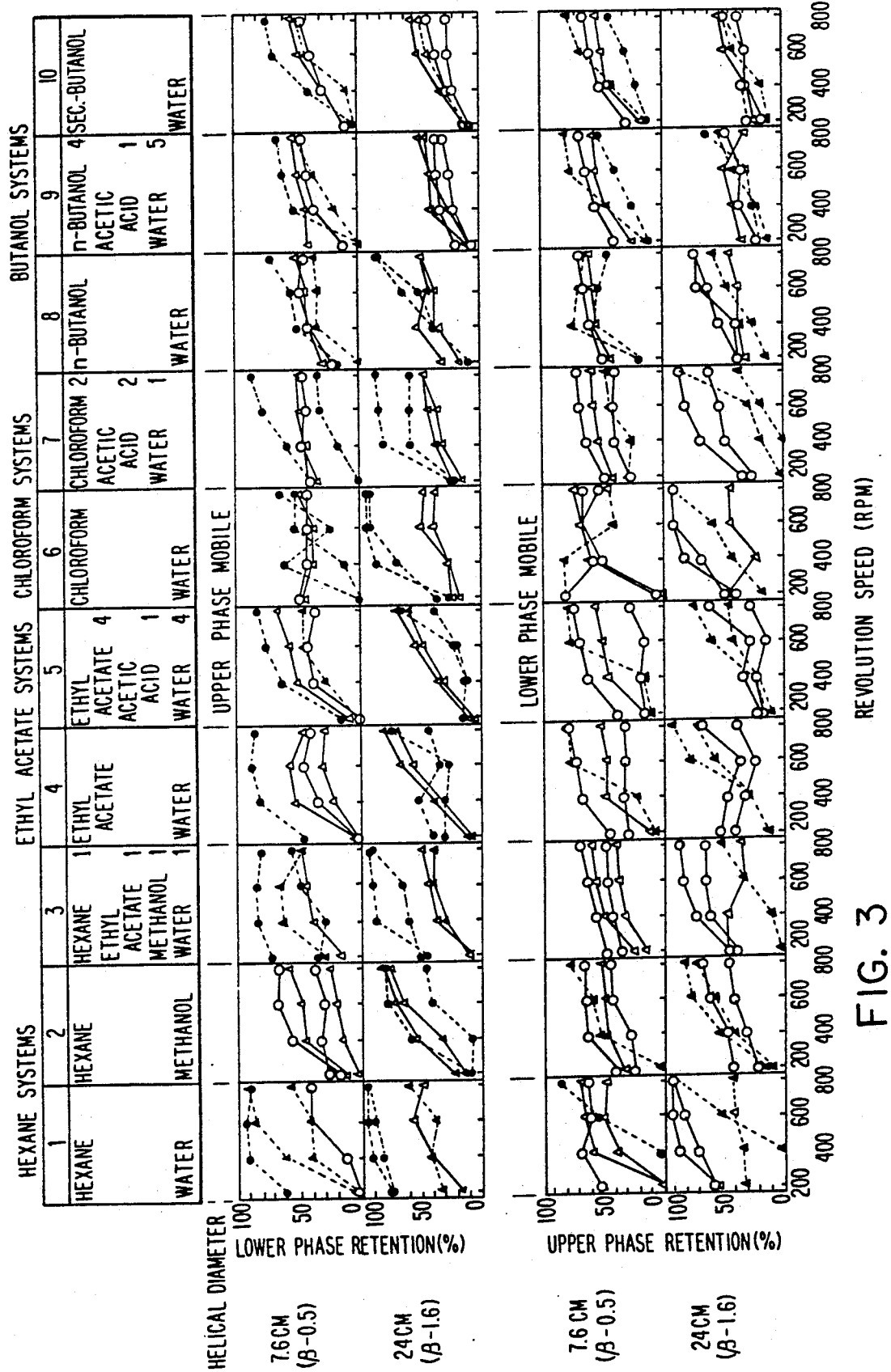
FIG. 3 is a set of phase retention diagrams for 10 pairs of two-phase solvent systems in two helical diameter coils of a XLL coil planet centrifuge.

In this example, runs were performed with ten different two-phase solvent systems (FIG. 3). At the maximum speed of 800 rpm, the retention of each phase was measured in each coil under eight different experimental conditions, i.e., all possible combinations of the planetary motion ($P_I$ and $P_{II}$), the head-tail elution mode (head to tail and tail to head), and the inward-outward elution mode determined by the handedness of the coil (right-handed and left-handed) as indicated in Table I, below.

TABLE I
EIGHT DIFFERENT ELUTION MODES IN X-AXIS CPC

| PLANETARY MOTION | HEAD-TAIL ELUTION MODE | INWARD-OUTWARD ELUTION MODE (HANDEDNESS OF COIL*) | COMBINED ELUTION MODE** | SYMBOLIC SIGNS IN PDD*** |
|---|---|---|---|---|
| $P_I$ | HEAD → TAIL | INWARD (R) | $P_I$-H-I | ○—○ |
|  | HEAD → TAIL | OUTWARD (L) | $P_I$-H-O | ○—● |
|  | TAIL → HEAD | INWARD (L) | $P_I$-T-I | ●—● |
|  | TAIL → HEAD | OUTWARD (R) | $P_I$-T-O | ●—● |
| $P_{II}$ | HEAD → TAIL | INWARD (L) | $P_{II}$-H-I | △—△ |
|  | HEAD → TAIL | OUTWARD (R) | $P_{II}$-H-O | △—▲ |
|  | TAIL → HEAD | INWARD (R) | $P_{II}$-T-I | ▲--▲ |
|  | TAIL → HEAD | OUTWARD (L) | $P_{II}$-T-O | ▲--▲ |

*R: RIGHT-HANDED; L: LEFT-HANDED
**H: HEAD → TAIL; T: TAIL → HEAD; I: INWARD; O: OUTWARD
***PDD: PHASE DISTRIBUTION DIAGRAM

Choosing two best conditions which produced high retention of the stationary phase in each handedness of the coil at 800 rpm, the retention was further measured under the reduced rpm (600, 400 and 200) to obtain the phase retention diagram illustrated in FIG. 3 and described below. Generally, it was discovered that a rotational speed of about 600 to about 1000 rpm was suitable for purposes of the present invention.

From each run, retention of the stationary phase was expressed as a percentage relative to the total column capacity according to the expression $100(V_C+V_F-V_S)/V_C$, where $V_C$ is the total capacity of the coil; $V_F$ is the free space in the flow tubes; and $V_S$ the volume of the stationary phase eluted from the coil. From these retention data the hydrodynamic distribution of the two solvent phases in the coil was summarized in a phase retention diagram constructed by plotting percentage retention of the stationary phase as a function of revolutional speed for each mobile phase. A group of retention curves produced by different elution modes but otherwise identical experimental conditions can be illustrated in the same diagram. In order to distinguish each elution mode in the phase retention diagram, a set of symbolic designs was used to draw phase retention curves as illustrated in Table I.

FIG. 3 illustrates a set of phase retention diagrams for the 10 different two-phase solvent systems with a broad range in hydrophobicity. Each column in FIG. 3 was obtained from the solvent system indicated at the top and arranged from left to right according to the degree of hydrophobicity of the major organic component. The upper panel in FIG. 3 shows the retention of the lower stationary phase and the lower panel shows the retention of the stationary upper phase In each panel, the first row was obtained from the coil mounted on the 7.6 cm diameter holder ($\beta=0.5$) and the second row from the coil mounted on the 24 cm diameter holder ($\beta=1.6$) as indicated on the left margin.

In each diagram, four retention curves are drawn against the applied revolution speeds from 200 rpm to 800 rpm. Among those four curves, two were obtained from the right-handed coil and the other two from the left-handed coil, both groups being selected among 4 possible combinations of the elution modes (see Table 1 for symbolic designs assigned for each elution mode). In general, 50% retention is considered satisfactory, but at higher retention, better peak resolution is expected.

The results show that the majority of the retention curves rise with increased rpm approaching a plateau at the highest speed of 800 rpm. All solvent systems showed a satisfactory phase retention of 50% or greater at 800 rpm, regardless of the choice of the mobile phase or $\beta$ values. The most important finding from these results is that the hydrophilic and low interfacial tension solvent systems such as n-butanol/acetic acid/water (4:1:5) and sec.-butanol/water show excellent phase retention ranging from 65% to 80% in the 7.6 cm helical diameter coil ($\beta=0.5$). These retention figures substantially exceed those previously obtained from the existing X-axis CPC including types X, XXL, and XL.

In the present example, the retention volume of the stationary phase was measured after the elution volume exceeded the total column capacity so that solutes with $K(Cm/Cs) \geq 1$, if introduced at the beginning of the experiment, would be eluted before the end of the experiment. Here, $K(Cm/Cs)$ is the partition coefficient given by solute concentration in the mobile phase divided by that in the stationary phase.

The majority of the retention diagrams illustrated in FIG. 3 show that the left-handed coil (thin lines) gives the highest retention levels especially in the 7.6 cm helical diameter coils. The comparison between the upper and lower panel reveals that two particular combinations of the elution mode dominate in each group, i.e., $P_I$-T-I and $P_{II}$-H-I in the upper panel and $P_{II}$-T-O and $P_I$-H-O in the lower panel (see Table I for symbols), indicating that the inward-outward elution mode plays a more significant role than the head-tail elution mode in the retention of the stationary phase. It is important to note that all the optimum conditions were discovered to be solely provided by use of left-handed coils.

In practical use the multilayer coil column as shown in FIG. 2 usually consists of right-handed and left-handed coils alternating in each layer. In this configuration, efficient separations are obtained only if each coiled layer retains a satisfactory volume of the stationary phase at a given elution mode. However, the present experimental results clearly indicate that left-handed coils generally yield much higher retention levels than right-handed coils. In order to make the most use of this discovered hydrodynamic trend, it was determined that the configuration of the conventional multilayer coil should be modified in such a way that all layers are also exclusively left-handed. This can be either done by connecting each layer with a narrow transfer tube or using a continuous piece of tubing which is directly returned to the starting position after completing each coiled layer. Although this modification would cause minor deformation of the multilayer coil by accommodating the connection flow tube between each layer, it nevertheless has been discovered that the modification provides good retention of the stationary phase of viscous polar solvent systems such as butanol which tend to produced carryover problems in other types of the CCC apparatus. Because of the excellent phase retention obtained from the most viscous sec.-butanol/water solvent system tested in this example, the apparatus was further modified and tested, as discussed below utilizing aqueous-aqueous polymer phase systems.

EXAMPLE 2

In this example, the capability of a modified XLL CPC was evaluated in separation of four proteins, including cytochrome C, myoglobin, ovalbumin and hemoglobin, with an aqueous-aqueous two-phase solvent system. The partition coefficients (K) of these proteins were optimized by choosing a polymer phase system composed of 12.5% (w/w) polyethylene glycol (PEG) 1000 and 12.5% (w/w) anhydrous di-basic potassium phosphate in water. The separations were performed in a pair of multilayer coils coaxially mounted around the column holders with 3.8 cm hub diameters. From the obtained chromatograms, performance of the system was evaluated in terms of theoretical plate number, peak resolution, separation speed, etc.

This example utilized a pair of spool-shaped coil holders each measuring 3.8 cm in hub diameter and 5 cm in width between the pair of flanges. A multilayer coil was mounted on each holder by winding a 2.6 mm ID PTFE (polytetrafluoroethylene) tube directly onto the holder hub making 5 layers of left-handed coils. All coiled layers were connected in series by bridging each neighboring layer across the width of the column with a piece of small-bore PTFE transfer tubing (0.7 mm ID) using a short sheath of intermediate-size tubing (1.6 mm ID) as an adapter.

The aqueous-aqueous two-phase polymer system utilized in this example was prepared by dissolving 150 g of polyethylene glycol 1000 and 150 g of anhydrous mono- and di-basic potassium phosphate in 900 g of distilled water. The solvent mixture was thoroughly equilibrated in a separatory funnel at room temperature and the two phases were separated shortly before use.

The partition coefficients of the four protein samples were determined in the two-phase solvent system composed of 12.5 or 16% (w/w) PEG 1000 and 12.5% (w/w) potassium phosphate where the ratio between mono- and di-basic varied from 1 to 3. About 5 mg of each protein was partitioned in 3 ml of the aqueous polymer two-phase system (1.5 ml each of the upper and lower phases). A 0.5 ml aliquot of each phase was diluted with water and the absorbance was measured at 280 nm with a Zeiss PM 6 spectrophotometer. The sample solution consisted of 10 mg of cytochrome C (horse heart), 20 mg of myoglobin (horse heart), 120 mg of ovalbumin (chicken egg) and 30 mg of hemoglobin (bovine) dissolved in 2 ml of the above solvent system consisting of equal volumes of each phase.

In this example, the entire column was initially filled with the stationary upper phase. This was followed by sample injection through the sample port. Then, the apparatus was rotated at 750 rpm while the mobile lower phase was pumped into the column at a flow-rate of 1.0 ml/min in the proper elution mode. The effluent from the outlet of the column was continuously monitored with an LKB Uvicord S (LKB Instruments, Uppsala, Sweden) at 280 nm and then fractionated into test tubes (3 ml/tube) with an LKB Ultrorac fraction collector (LKB Instruments). After three peaks were eluted, the upper phase was pumped in the reversed direction (by switching the inlet and outlet of the column) to elute the hemoglobin which was retained in the column. An aliquot of each fraction was diluted with distilled water and the absorbance was determined at 280 nm with a Zeiss PM 6 spectrophotometer.

Figure 4:
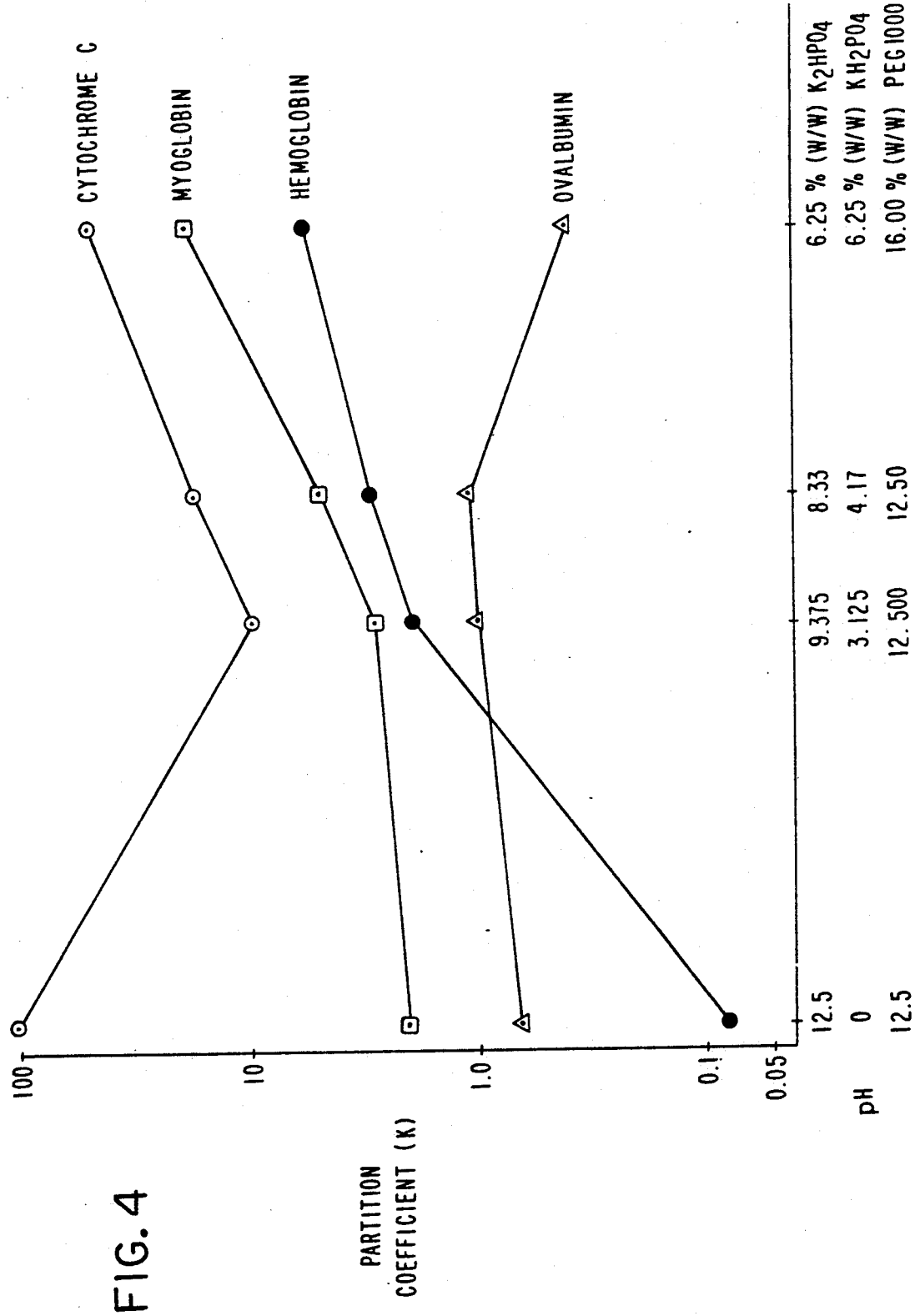
FIG. 4 is a graph illustrating the effects of potassium phosphate compositions on partition coefficients ($K=C_L/C_C$) of four protein samples in a polymer phase system composed of 12.5%(w/w) PEG 100 and 12.5%(w/w) anhydrous potassium in water. (Partition coefficient is expressed by protein concentration in the lower phase divided by that in the upper phase).

FIG. 4 shows the partition coefficient values ($K = C_L/C_U$) of the four proteins plotted in a logarithmic scale against the various compositions of monobasic and di-basic potassium phosphates in the polymer phase. The partition coefficients of these proteins generally increase as the relative amount of di-basic potassium phosphate decreases while increased concentrations of the mono-basic potassium phosphate to the di-basic above the 1:1 ratio resulted in formation of a single phase. An evenly scattered ideal distribution of the four partition coefficient values is observed in the solvent system composed of 12.5% di-basic potassium phosphate and 12.5% PEG 1000.

Figure 5:
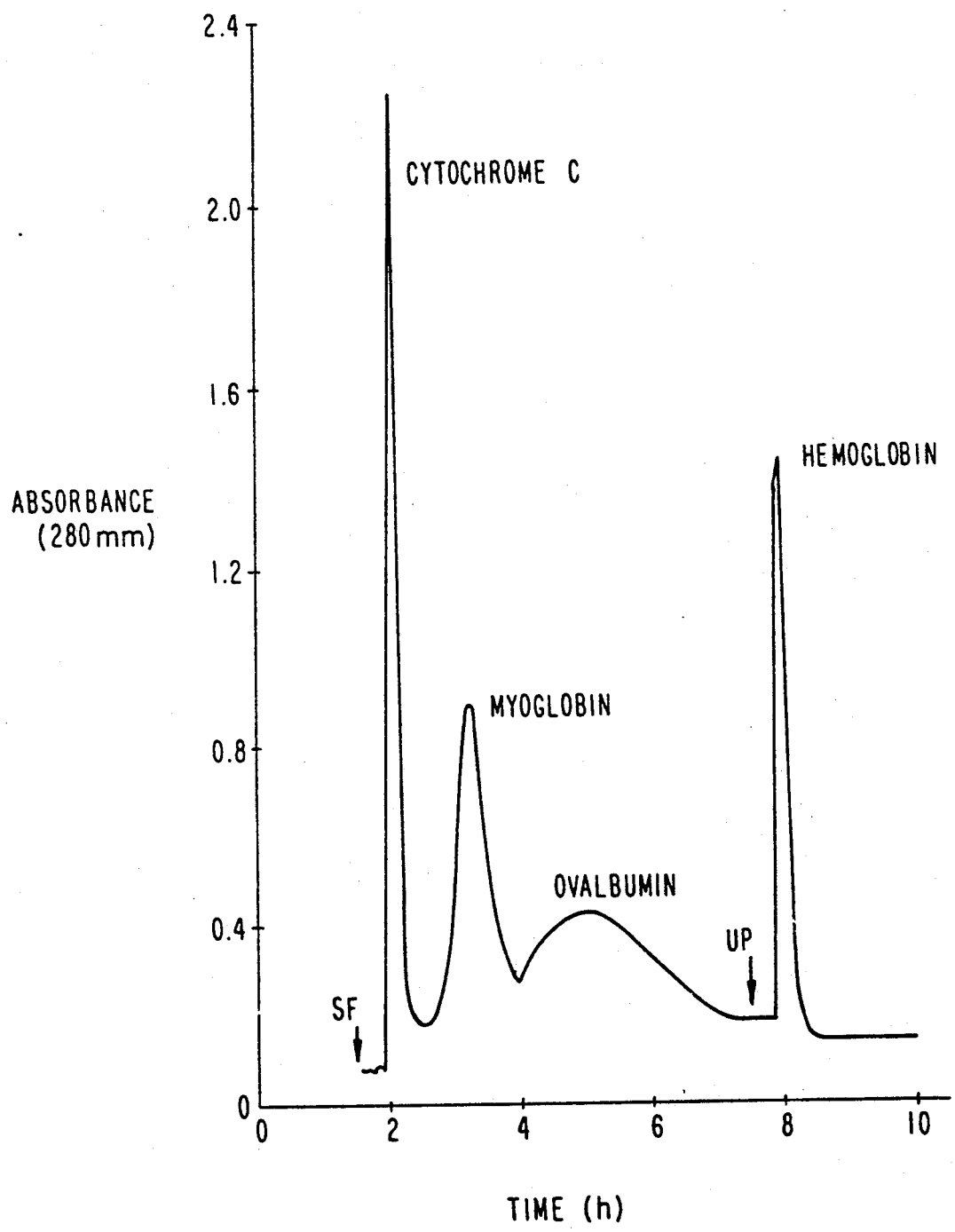
FIG. 5 is a chromatograph of four protein samples with the polymer system composed of 12.5%(w/w) PEG 1000 and 12.5%(w/w) anhydrous dibasic potassium phosphate in distilled water. The sample size included 10 mg cytochrome C, 20 mg myoglobin, 120 mg ovalbumin, and 30 mg hemoglob. The flow rate was 1 ml/min. and the revolution speed was 750 rpm.

FIG. 5 shows a chromatogram of cytochrome C, myoglobin, ovalbumin and hemoglobin obtained with the aqueous-aqueous polymer phase system. The proteins were eluted from the column in the order of their partition coefficient values, $K(C_L/C_U)$, within 8.5 hours After the elution of cytochrome C ($K = 103.7$), myoglobin ($K = 2.08$) and ovalbumin ($K = 0.63$), the PEG-rich upper phase was pumped into the column in the reversed direction to facilitate rapid elution of the hemoglobin ($K = 0.08$) still remaining the column. The fractions containing cytochrome C, myoglobin and hemoglobin were easily identified by their colors, i.e., red, yellow and brown, respectively.

The column efficiency in separation was expressed in peak resolution, Rs, using the conventional equation $Rs = 2(R_2 - R_1)/(W_1 + W_2)$, where $R_1$, $R_2$ are retention time (or volume) of two adjacent peaks; $W_1$ and $W_2$, the peak width of the same peaks expressed in the same unit as $R_1$ and $R_2$. The peak resolution determined from the above equation are 1.67 between cytochrome C and myoglobin and 0.62 between myoglobin and ovalbumin. After the elution of these three proteins, the volume of the upper stationary phase retained in the column was 52.4% of the total column capacity (250 ml).

Aqueous-aqueous polymer phase systems are known to be useful for the partition of macromolecules, including proteins, nucleic acids and polysaccharides, etc. However, high viscosity and low interfacial tension between the two phases tend to delay the phase separation. Although various types of the countercurrent chromatographic apparatus have been introduced to overcome this problem, the amount of the stationary phase retained in the column is extremely limited unless the flow rate of the mobile phase is reduced, which is turn results in unacceptable long separation times.

As described above, the results of the studies conducted in the course of the present invention provide a new configuration for the multilayer coil columns used in a XLL coil planet centrifuge. The modified type-XLL X-axis CPC utilized according to the present invention provides satisfactory retention of the stationary phase at relatively high flow rate of the mobile phase, thus facilitating the efficient use of the aqueous-aqueous polymer phase systems for separation of biopolymers.

Although the invention has been described with reference to particular means, materials and embodiments, from the foregoing description, one skilled in the art can ascertain the essential characteristics of the present invention and various changes and modification may be made to adapt the various uses and characteristics thereof without departing from the spirit and scope of the present invention as described in the claims which follow.

We claim:

1. In a cross-axis synchronous flow-through coil planet centrifuge including a pair of column holders mounted on each side of a rotary frame and a pair of multi-layered coil columns mounted on said column holders, the improvement wherein each of said pair of coiled columns consists of left-handed coils.

2. A cross-axis synchronous flow-through coil planet centrifuge according to claim 1, wherein said centrifuge has a degree of lateral shift of at least 2.

3. A cross-axis synchronous flow-through coil planet centrifuge according to claim 1, wherein adjacent coil layers of said multi-layered coil columns are connected together through a transfer tube.

4. A cross-axis synchronous flow-through coil planet centrifuge according to claim 1, wherein each of said pair of multi-layered coil columns consist of a continuous piece of tubing.

5. A cross-axis synchronous flow-through coil planet centrifuge according to claim 1, wherein each of said column holders has a diameter of from about 3.8 cm to about 24 cm.

6. A cross-axis synchronous flow-through coil planet centrifuge according to claim 7, wherein each of said pair of multi-layered coil columns comprises five layers of coil.

7. A method of partitioning macromolecules utilizing a cross-axis synchronous flow-through coil planet centrifuge which comprises:
providing a cross-axis synchronous flow-through coil planet centrifuge with multi-layered coil columns which consists of left-handed coils;
providing an aqueous-aqueous tow-phase solvent system including a stationary phase and a mobil phase;
filling said centrifuge with said stationary phase of said aqueous-aqueous two-phase solvent system;
injecting a sample containing macromolecules into said centrifuge;
supplying said mobil phase of said aqueous-aqueous two-phase solvent system to said centrifuge while rotating said centrifuge; and
eluting said macromolecules from said sample.

8. A method of partitioning macromolecules according to claim 9, wherein said aqueous-aqueous two-phase solvent system comprises an aqueous-aqueous polymer phase system.

9. A method of partitioning macromolecules according to claim 11, wherein said centrifuge is rotated at from about 600 to 1000 rpm.

10. A method of partitioning macromolecules according to claim 9, wherein said macromolecules comprise biopolymers.

11. A method of partitioning macromolecules according to claim 12 wherein said biopolymers are selected from the group consisting of proteins, nucleic acids, polysaccharides, and mixtures thereof.

12. A method of partitioning macromolecules according to claim 13, wherein said aqueous-aqueous two-phase solvent system comprises polyethylene glycol and potassium phosphate.

13. A method of partitioning macromolecules according to claim 13, wherein said aqueous-aqueous two-phase solvent system comprises polyethylene glycol and sodium phosphate.

14. A method of partitioning macromolecules according to claim 12 wherein said biopolymers are selected from cells and cell organelles.

* * * * *